(12) United States Patent
Bareiss et al.

(10) Patent No.: US 8,607,652 B2
(45) Date of Patent: Dec. 17, 2013

(54) APPARATUS FOR HANDLING A LIQUID SAMPLE

(75) Inventors: Karl-Heinz Bareiss, Lorch (DE); Michael Kirchner, Nurtingen (DE); Ralf Steuerwald, Ederdingen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 590 days.

(21) Appl. No.: 12/923,177

(22) Filed: Sep. 8, 2010

(65) Prior Publication Data

US 2011/0056312 A1 Mar. 10, 2011

(30) Foreign Application Priority Data

Sep. 8, 2009 (DE) ...................... 20 2009 012 165 U

(51) Int. Cl.
*G01N 1/14* (2006.01)
(52) U.S. Cl.
USPC .................. 73/864.35; 73/863.11; 73/864.34
(58) Field of Classification Search
USPC ................ 73/863.11, 864.34, 864.35, 864.73
See application file for complete search history.

(56) References Cited

U.S. PATENT DOCUMENTS

| | | | | |
|---|---|---|---|---|
| 2,348,806 A | * | 5/1944 | Gillard et al. .............. | 73/863.11 |
| 3,795,347 A | * | 3/1974 | Singer ........................ | 73/864.35 |
| 6,453,759 B1 | * | 9/2002 | Lebski et al. .............. | 73/864.34 |
| 6,880,413 B2 | * | 4/2005 | Zeller ......................... | 73/863.11 |
| 7,430,930 B2 | * | 10/2008 | Zeller et al. ................ | 73/864.34 |

FOREIGN PATENT DOCUMENTS

WO WO 2007/057432 * 5/2007

* cited by examiner

*Primary Examiner* — Daniel S Larkin
(74) *Attorney, Agent, or Firm* — Bacon & Thomas, PLLC

(57) ABSTRACT

An apparatus for handling a liquid sample, especially for automatic removal of a liquid sample from a sample-taking location, comprising: a control unit; a sample collecting unit; a supply and metering system, which is embodied to convey a liquid sample from the sample-taking location and to meter the sample into a liquid receptacle of the sample collecting unit; a housing with a first housing part, which at least partially surrounds at least the sample collecting unit, and a second housing part, which is separated from the first housing part, and which at least partially surrounds a metering space; wherein at least parts of the supply and metering system are arranged in the metering space; and wherein the apparatus furthermore includes a plate, which is releasably connected with the second housing part surrounding the metering space, and which divides the metering space into a first metering space part and a second metering space part.

14 Claims, 8 Drawing Sheets

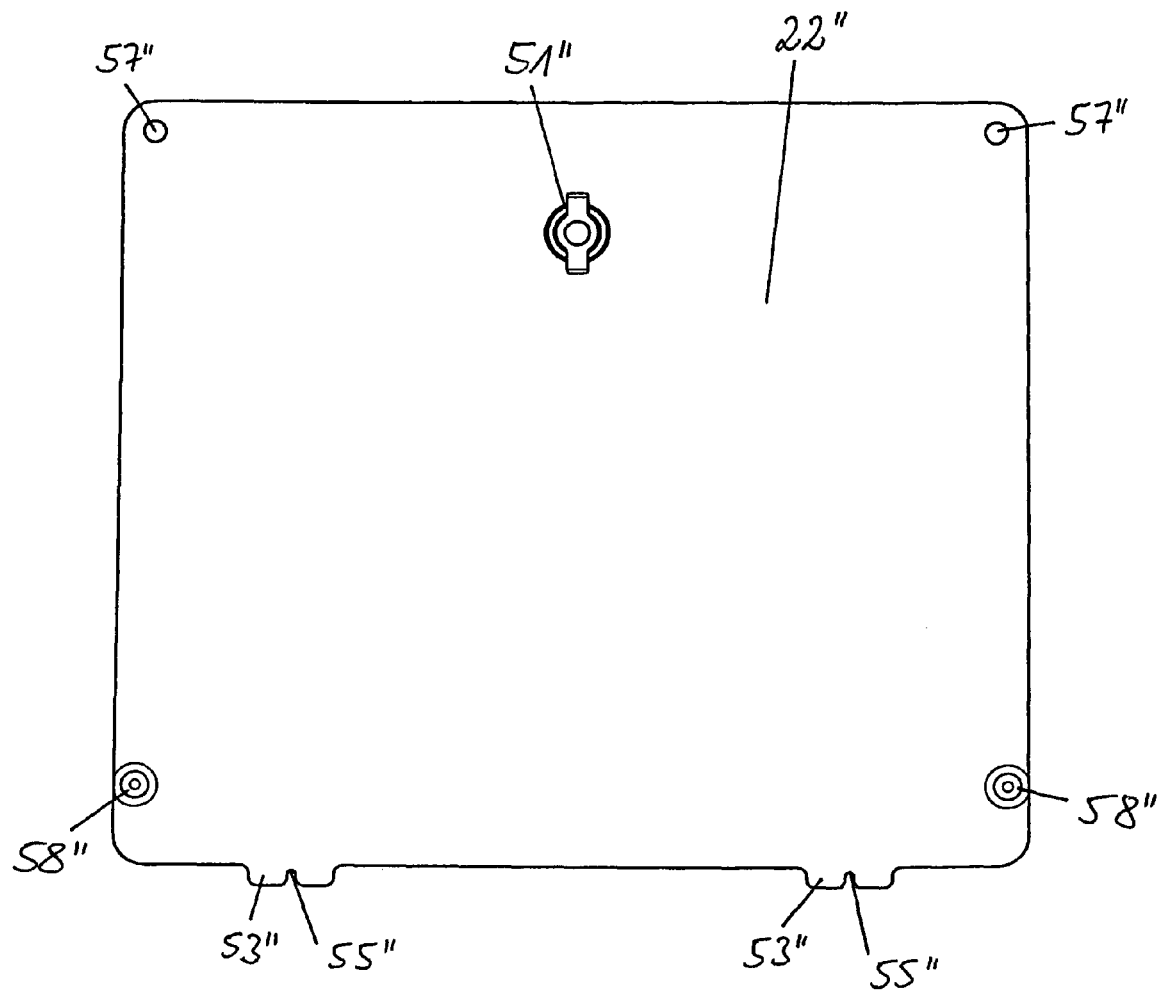

APPARATUS FOR HANDLING A LIQUID SAMPLE

TECHNICAL FIELD

The invention relates to an apparatus for handling a liquid sample, especially for automatic removal of a liquid sample from a sample-taking location.

BACKGROUND DISCUSSION

In process measurements technology or in industrial measurements technology, apparatuses for handling liquid samples, especially for automatic removal of a liquid sample from a sample-taking location, are especially used for monitoring the quality of applied or manufactured liquids and liquid mixtures. Examples of such apparatuses are automatic sample takers, which, at predetermined points in time, withdraw from the sample-taking location a liquid sample with a predetermined volume, and collect this in sample containers. The collected samples can later be further examined and analyzed in the laboratory. Sample takers are also frequently used when monitoring and optimizing the cleaning effectiveness of a clarification plant, when monitoring activation basins and the clarification plant outlet or for controlling filler metering.

Besides a sufficient metering accuracy, the most important requirements for so-applied apparatuses, especially automatic apparatuses, for handling of liquids—especially automatic sample takers—are robustness, ease of operation and the assurance of sufficient working and environmental safety. At the same time, the effort involved and especially the costs for manufacture and maintenance of such apparatuses should be kept as low as possible, even though such apparatuses, as a rule, make use of a large number of individual components.

Known in the state of the art are modularly embodied apparatuses for handling liquid samples, especially for removal of liquid samples from a sample-taking location. The modular construction is intended to make the apparatuses robust and flexible in form. At the same time, a modular construction facilitates the manufacture of such apparatuses, and permits a retrofitting of an existing apparatus through addition of further modules with new functionalities.

In the international publication WO 2007/057432 A1, a modularly constructed sample taker is described, which can optionally be expanded with an analysis module, and thus is retrofittable to an automatic analysis device. A cooling/temperature control module is also provided, which, like the analysis module, can be embodied as a retrofittable, modular, structural unit. The temperature control module is accommodated in a module housing, which, by means of an adapter unit (which can, for example, be composed of mutually engaging, push-in rails) can be releasably connected with the housing of the sample taker.

The sample taker described in WO 2007/057432 A1 includes, as supply and metering system, a sample withdrawal unit, which is composed of at least a suction hose, a pump and a distributor station for the liquids which are supplied by means of the pump. The sample withdrawal unit can likewise be embodied as a module. The sample withdrawal unit is a component of a wet space, which is separated from additional modules. As a component of the wet space (which forms, as a whole, one module), the sample withdrawal unit cannot easily be replaced with another sample withdrawal unit (for example, with a sample withdrawal unit which works according to another functional principle). This would mean a certain effort for modification of the wet space module.

SUMMARY OF THE INVENTION

An object of the invention is to provide an apparatus for handling a liquid sample—especially for automatic removal of a liquid sample from a sample-taking location—which apparatus has diverse applicability, and which, especially, is simultaneously robust and user friendly.

This object is achieved by an apparatus for handling a liquid sample, especially for automatic removal of a liquid sample from a sample-taking location, comprising:
A control unit;
a sample collecting unit;
a supply and metering system which is embodied to convey a liquid sample from the sample-taking location and to meter this sample into a liquid receptacle of the sample collecting unit;
a housing, with a first housing part, which at least partially surrounds at least the sample collecting unit, and a second housing part, which is separated (especially by a partition) from the first housing part, and which at least partially surrounds a metering space;
wherein at least parts of the supply and metering system are arranged in the metering space; characterized in that,
the apparatus furthermore includes a plate, which is releasably connected with the second housing part surrounding the metering space, and which divides the metering space into a first metering space part and a second metering space part.

The supply and metering system can be embodied differently, depending on the field of application, and consequently can have different components. As explained below in more detail, a supply and metering system of a sample taker can, for example, be embodied according to the peristaltic principle or according to the vacuum principle. The supply and metering system can also include a media line (which is under pressure, and which is arranged outside of the metering space, and especially outside of the housing of the apparatus), from which the liquid sample is to be withdrawn. In this case, as part of the supply and metering system, a valve mechanism can, for example, be arranged in the metering space, wherein this valve mechanism can produce and subsequently sever a connection to the pressure tube.

Since the metering space of the apparatus, in which at least parts of the supply and metering system are arranged, is divided in two metering space parts by means of a plate which is releasably connected with the housing surrounding the metering space, various options emerge concerning the arrangement of individual components of the supply and metering system. For example, components of the supply and metering system can be separated from one another by means of the plate, e.g. liquid contacting components (such as liquid lines) can be separated from electrical/mechanical components (such as pump drives). It is also possible to accommodate together in one of the metering space parts all supply and metering system components requiring maintenance. In this way, only one of the two metering space parts must be embodied so as to be easily accessible for operating personnel. Another opportunity which the apparatus of the invention offers lies in the ability to secure components of the supply and metering system on the plate. Individual components of the supply and metering system can then, for example, be secured on the plate, and other components on the housing wall of the housing, which surrounds the metering space. This offers a number of options for accommodating the supply and metering system in the metering space with an optimal utilization of space. Finally, the plate which is releasably connected with the housing can also serve as the base plate of a module for a modularly embodied apparatus. For forming such a module, all or at least some of the components of the supply and metering system can be secured on the plate. The plate with the components can then be connected by the manufacturer or by the user of the apparatus with the additional modules of the apparatus via the releasable connection with the metering space housing. Through the manifold options for embodiment available, the apparatus has diverse applications. At the same time, the described plate fits very well into a modular sample-taker concept, e.g. according to WO 2007/057432 A1.

The apparatus can especially be an automatic sample taker of the previously described type.

In an advantageous embodiment, the plate completely covers the second metering space part. In this case, there can be arranged in the second metering space part such components of the supply and metering system which do not so frequently have to be subjected to maintenance by service personnel (and, consequently, do not have to be so easily accessible), or which should be especially well-protected from environmental influences (especially from moisture or dust) or from unauthorized accessing. This makes the sample taker, as a whole, more robust.

In an especially advantageous embodiment, at least parts of the supply and metering system (i.e. a portion of the components, of which the supply and metering system is formed) are secured on the plate. All components which are secured on the plate can thus be installed in the apparatus in a single installation step—namely by connecting the plate with the housing part which surrounds the metering space—and can correspondingly be removed again from the apparatus by releasing the connection. This is not only of advantage in the case of manufacturing the apparatus, but can also be utilized by the user of the apparatus, in order, for example, to retrofit the apparatus with a new supply and metering system, or in order to withdraw the components of the supply and metering system from the housing for maintenance purposes. This facilitates serviceability.

In an additional embodiment, other components of the supply and metering system (especially those which are not connected with the plate)—especially a vacuum pump or a valve mechanism for removal of liquid from a media line which is under pressure and which is arranged outside of the metering space—can be arranged in the second metering space part. In this case, the plate, together with the housing part which surrounds the second metering space part of the apparatus, serves as protection (e.g. from environmental influences or unauthorized accessing) for the components arranged therein.

The plate can, advantageously, be connected via an interface with the second housing part surrounding the metering space part, wherein the interface includes at least three mounting points, wherein at least two mounting points are embodied as guiding means, which engage with complementary guiding means, which are firmly connected with the housing, and which are formed in an inner wall of the second housing part. The third mounting point can be formed by a pivotable rotary latch, which engages behind a catch, which is formed by the inner wall of the metering space or secured on the inner wall. The catch can be formed by a protrusion of the housing wall, behind which the rotary latch can pivot. The catch can also be a cavity in the wall, into which the rotary latch can pivot. The two guiding means can, for example, be embodied as protrusions on a plate side, which each have a groove, which can be made to engage with (especially rail-like) guiding means (which are complementary to the groove) inside the second housing part, so that the plate can pivot about an imaginary rotation axis, which extends along the plate side with the protrusions. In order to connect the plate with the second housing part, the grooves of the protrusions are made to engage with the complementary (especially rail-like) guiding means, and the plate is pivoted into its end position, in which it is fixed by pivoting the rotary latch behind the protrusion of the inner wall of the second housing part.

Additionally, the plate can be supported floatingly relative to the inner wall of the second housing part in at least two additional mounting points via parabolic buffers. The parabolic buffers serve for oscillation decoupling of the plate from the remaining housing of the apparatus.

The plate can be embodied as a deep drawn part, which has a relief structure, which is matched to the shape of the parts of the metering and supply system secured to the plate. For example, the relief structure can comprise a gutter-like recess, in which a liquid line of the supply and metering system—for example, a hose of a peristaltic pump—is embedded and held.

The supply and metering system can comprise, for example, a peristaltic pump or a vacuum pump.

In a preferred embodiment, the sample collecting system is arranged in a separate sample collecting space, which lies opposite the metering space, from which it is separated especially by a partition. The sample collecting space can be embodied especially as a module releasably connected with the second housing part surrounding the metering space part. Such a modular construction offers a high flexibility, especially with regard to manufacture of the apparatus.

For improving the metering accuracy, on the plate can furthermore be secured a media detector (especially one comprising a light barrier, a pressure sensor and/or a flow measuring device) for determining the volume (or a variable correlated therewith) of the liquid sample supplied by the supply and metering system.

The invention further includes a module-kit for manufacturing an apparatus according to one of he previously described embodiments, comprising: an electronics unit, which includes a control unit;

at least one sample collecting module having a first housing part which at least partially surrounds the sample collecting module, which especially is connected or connectable with additional housing parts to form a housing of the apparatus;

a plurality of sets of components of various types of supply and metering systems, wherein said sets of components include at least a set of components of a supply and metering system working according to the peristaltic principle, and a set of components of a supply and metering system working according to the vacuum principle;

at least a second housing part for forming a metering space, wherein the second housing part especially is connected or connectable with additional housing parts for forming a housing of the apparatus, a set of a plurality of differently embodied plates, each of which has an identically embodied interface for releasable connection of the plate with the second housing part to form the metering space, wherein differently embodied plates have different relief structures, in order to accommodate different components or combinations of components of a supply and metering system and to secure these to the plate;

The identically embodied interfaces comprise, for example, three mounting points, wherein at least two mounting points are embodied as guiding means, which can be made to engage with complementary guiding means, which are firmly connected with the second housing part to form the metering space. The third mounting point can be formed by a pivotable rotary latch. The two guiding means can be embodied, for example, as protrusions on a plate side, wherein the protrusions each have a, which can be made to engage with an (especially rail-like) guiding means in the second housing part complementary to the groove. Additionally, there can be provided as other mounting means elastic buffer elements (especially parabolic buffers) for floating support for the purpose of oscillatory isolation of the plate. Their number and arrangement is, however, not of importance; that is to say, identically embodied interfaces can also be arranged differently, or comprise differently many such elastic buffer elements.

BRIEF DESCRIPTION OF THE DRAWINGS

The invention will now be explained in greater detail on the basis of the appended drawing, the figures of which show as follows:

FIG. 8 is a schematically shown, detail view of the plate which subdivides the metering space of the sample taker of FIG. 7 into two metering space parts.

DETAILED DISCUSSION IN CONJUNCTION WITH THE DRAWINGS

Figure 1:
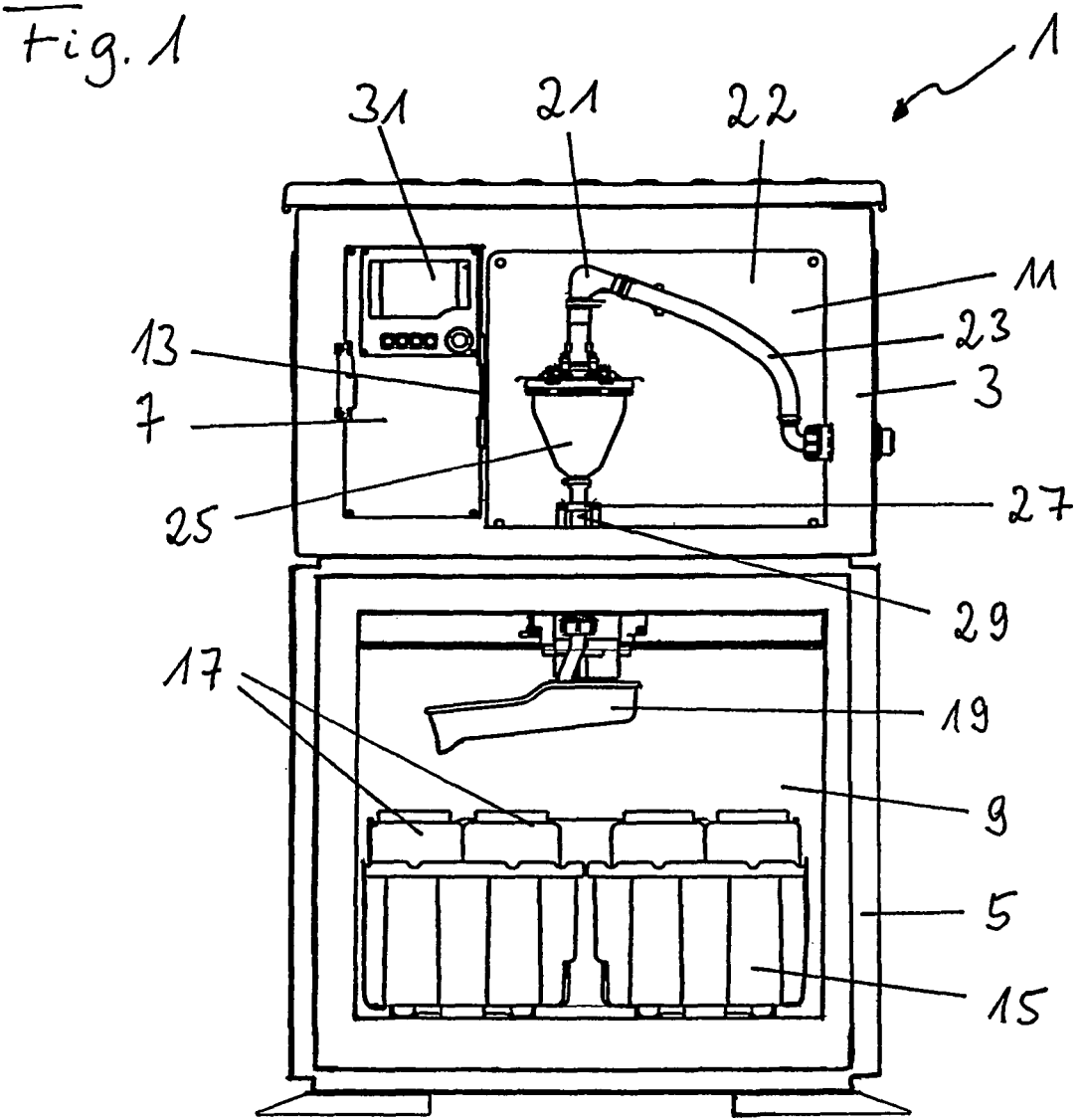
FIG. 1 is a schematically shown, total view from the front of a sample taker having a supply and metering system working according to the vacuum principle.
Figure 2:
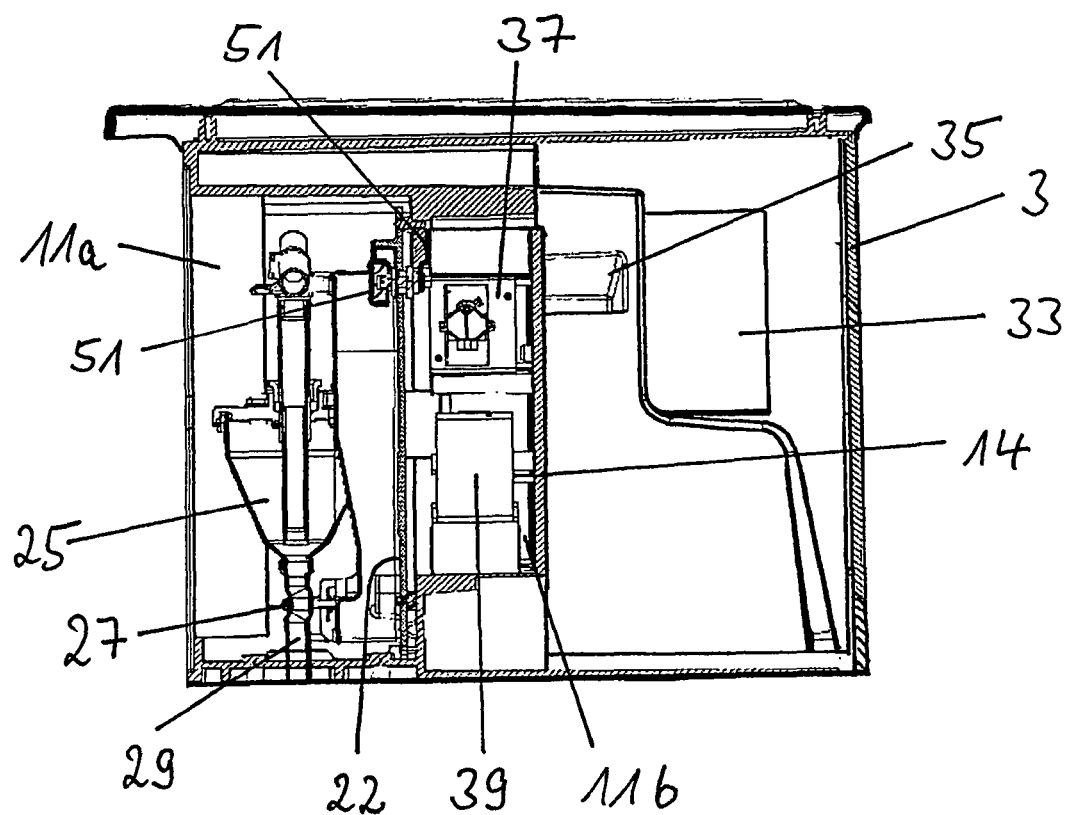
FIG. 2 is a schematically shown, total view in cross section of the upper housing part of the sample taker shown in FIG. 1.

FIGS. 1 and 2 show schematically an automatic sample taker 1 having an upper housing part 3 and a lower housing part 5, wherein the lower housing part 5 is separated by a partition from the upper housing part 3. FIG. 1 shows the sample taker 1 in a view from the front, and FIG. 2 shows the upper housing part 3 of the sample taker 1 in cross section. Accommodated in the upper housing part 3, are a metering space 11 and an electronics unit 7. Accommodated in the lower housing part 5 is the sample collecting space 9. Both the upper housing part 3 as well as the lower housing part 5 have, in each case, a door (not shown), which, in its closed state, seals the metering space 11 and the electronics unit 7, or the sample collecting space 9, as the case may be, off from the environment, and thus protects these parts from environmental influences. The doors can be opened for performing maintenance in the sample collecting space 9 or in the metering space 11, or for servicing the electronics unit 7.

The sample collecting space 9 contains two cases 15 for accommodating a plurality of sample collecting containers 17. The liquid samples, which are supplied via the supply and metering system 21 arranged in the metering space 11 and described in further detail below can be distributed into the sample collecting containers 17 via a pivotable, sample distributing arm 19.

The upper housing part 3 includes two partitions 13 and 14. Partition 14 bounds a rear housing region, in which a cooling unit 33 and an energy supply unit 35 are accommodated. The remaining front housing region of the upper housing part 3 includes the electronics unit 7 and the metering space 11, which are separated from one another by the partition 13.

Metering space 11 is bordered, in the example illustrated here, on five sides by the upper housing part 3 and the partition 13, which lies between the metering space and the electronics unit 7. By way of the already mentioned door, the upper housing part 3 of the metering space 11 can be closed off from the environment. In the metering space 11 is a plate 22, which, in the present example, serves to secure parts of a supply and metering system 21, which works according to the vacuum principle. Plate 22 is releasably connected with the inner housing wall of the housing part 3, which surrounds the metering space. Plate 22 divides the metering space 11 into a first (front) metering space part 11a, and a second (rear) metering space part 11b.

The supply and metering system 21 includes a suction line 23, through which liquid from the sample-taking location is sucked in with the assistance of a vacuum pump 39, which is secured on the rear-side (i.e. the side facing the second metering space part 11b) of the plate 22 in the second metering space part 11b (compare FIG. 2). Furthermore, the supply and metering system 21 includes a metering container 25 having a drain line 29, which can be blocked by a valve 27. Via a feed-through through the partition between the upper housing part 3 and the lower housing part 5, drain line 29 connects the metering container 25 with the sample distributor arm 19. At the beginning of a sample-taking, the metering container 25 is isolated by the valve 27. The vacuum pump 39 is then activated, and, via the suction line 23, a liquid sample is sucked in from the sample-taking location. The vacuum pump 39 is then deactivated, with the desired sample volume remaining in the metering container. The valve is then opened, and, via the sample distributor arm 19, the liquid sample is metered into the sample collecting containers 17 arranged in a sample collecting unit.

Suction line 23, metering container 25, valve 27 and drain line 29 are arranged in the front metering space part 11a, and secured on the plate 22. Behind the plate 22, in the second metering space part 11b, is arranged, in addition to the vacuum pump 39 (which is secured on the plate 22), also a pneumatic switching mechanism 37 (which is not secured to the plate 22). Construction and application of such a pneumatic switching mechanism for sample takers using a supply and metering system according to the vacuum principle is described in detail, for example, in European Patent EP 978 716 B1.

The electronics unit 7 includes a control unit 31 for controlling the sample taker, especially for controlling the vacuum pump 39, the pneumatic switching mechanism 37, the valve 27, the cooling unit 33 and the sample distributor arm 19. Through the partition between the upper housing part 3 and the lower housing part 5 (or through the partitions 13 and 14 of the upper housing part 3) are provided corresponding electrical feed-throughs, via which run electrical lines for connecting the control unit 31 with these components of the sample taker 1 that are to be controlled. Via a display and input system of the control unit 31, operating personnel can input orders or new data, and read out data and/or measured values from the control unit 31.

Figure 3:
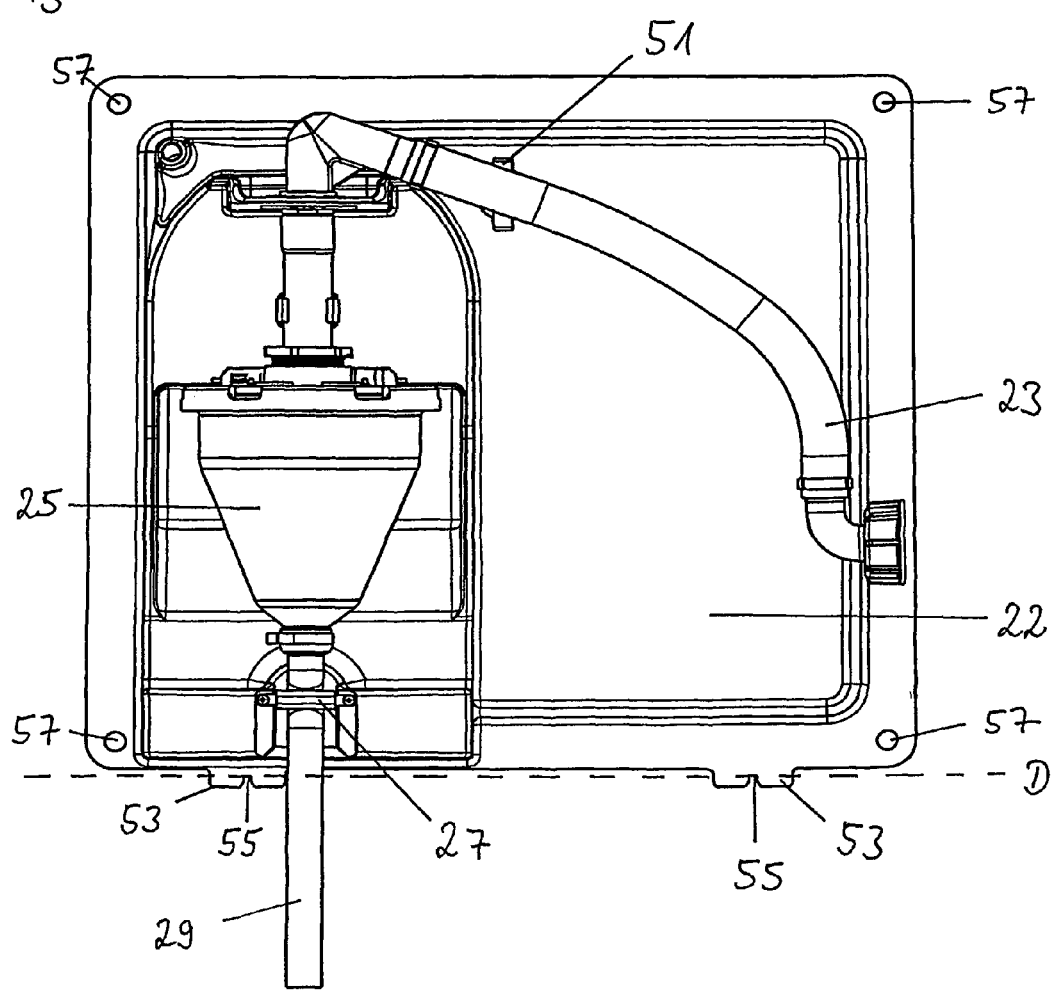
FIG. 3 is a schematically shown, detail view of the securement plate having the supply and metering system of the sample taker shown in FIG. 1.

FIG. 3 shows in detail the plate 22 serving in the present example as a securement plate. Visible are the components of the supply and metering system 21, which are secured on the front side of the plate. The plate 22 has a relief structure with depressions and raised portions. Components of the supply and metering system 21 are embedded in the depressions. For forming such a relief structure, the plate 22 can be manufactured, for example, by deep drawing. Thus; for example, the valve 27, which is embodied as a pinch valve, is arranged between two raised portions in the plate 22, and is secured to these. In FIG. 2, the section through the plate 22 is positioned in such a way, that the metering container 25, which is partially embedded into the relief structure, is in part hidden by the relief structure.

On one side, the plate 22 has two protrusions 53 extending in the plate plane. Each protrusion 53 has a groove 55. Protrusions 53 can be pushed into complementary cavities in the housing wall of the housing part which surrounds the metering space, wherein complementary guiding rails engage in the grooves 55. The complementary cavities or the guiding rails can be formed in a structure which is connected with the housing wall, or also be formed directly in the housing wall of the housing part 3.

When the two protrusions 53 are made to engage with the complementary guiding means in the housing wall of the housing part 3, the plate 22 can pivot about an imaginary rotation axis D along the plate side which has the protrusions 53. In order to affix the plate 22 firmly to the housing, in the vicinity of the plate side opposite the plate side with the projections 53 there is placed a rotary latch 51, which (as can also be seen in FIG. 2 in cross section) can pivot behind a protrusion of the metering space housing, which forms a catch. The protrusion of the metering space housing can be directly formed in the housing wall of the housing part 3, or also by a structure which is connected with the housing wall.

Plate 22 additionally has bores 57. If the plate is releasably connected by means of the protrusions 53 and the rotary latch 51 with the housing part 3 surrounding the metering space 11, the bores 57 serve as accommodations for elastic buffer elements, which effect an oscillation isolation of the plate 22 from the housing part 3 of the metering space 11. The buffer elements are preferably embodied as parabolic buffers (compare FIG. 6, as discussed below). Additionally, placed on the plate rear side (i.e. the side of the plate 22 facing the second metering space 11) can be other buffer elements, which, in an installed state of the plate 22, are pressed against a structure of the housing part 3 of the metering space 11. The protrusions 53, the rotary latch 51 and the buffer elements together form an interface for securing the plate 22 to the housing part 3 of the sample taker 1 surrounding the metering space 11.

Figure 4:
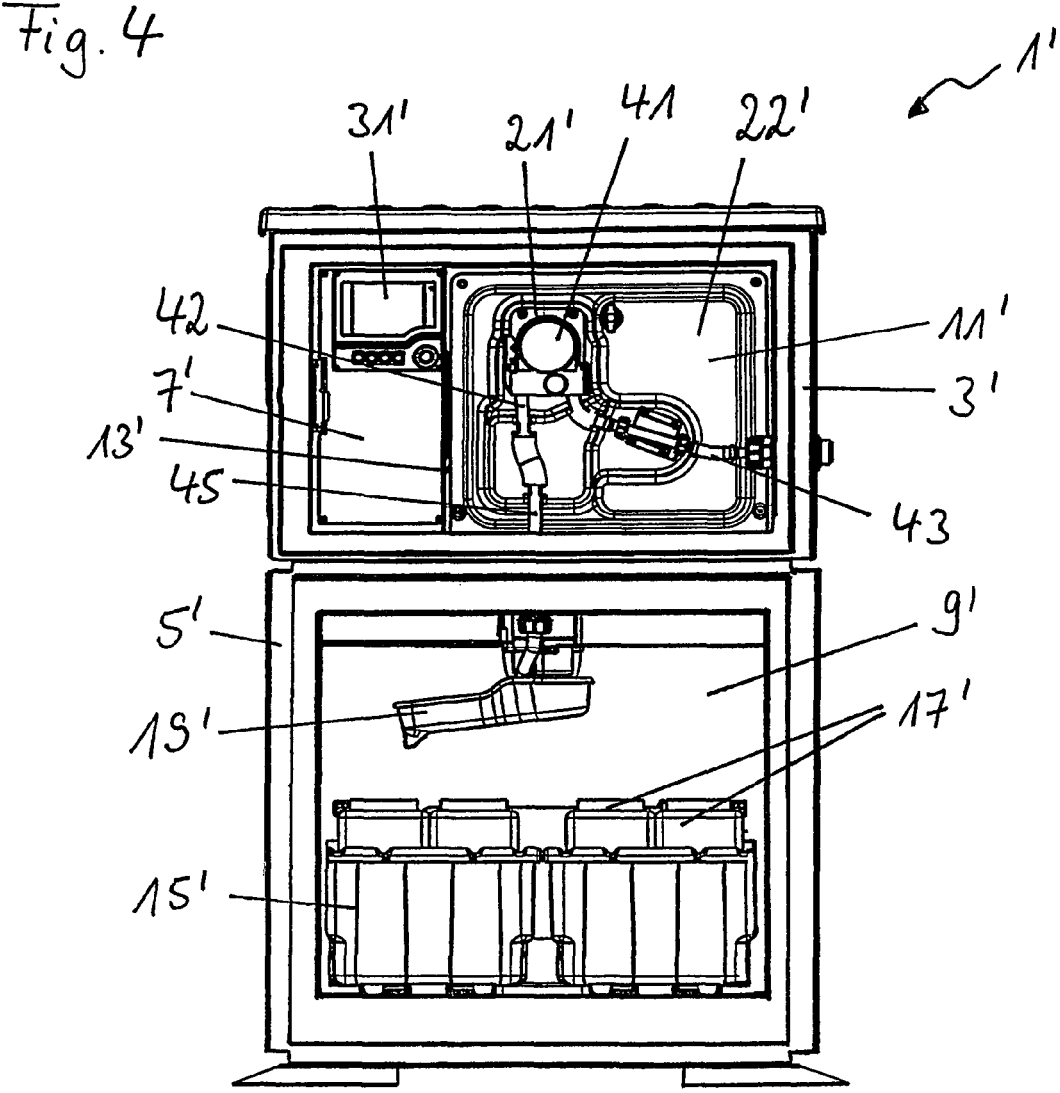
FIG. 4 is a schematically shown, total view from the front of a sample taker having a supply and metering system working according to the peristaltic principle.

FIG. 4 shows a total view from the front of an automatic sample taker 1' according to a second example of an embodiment. Sample taker 1' is, except for the supply and metering system 21', essentially equally constructed to the sample taker 1 of the first example of an embodiment, described on the basis of FIGS. 1 and 2. Sample taker 1' includes an upper housing part 3' and a lower housing part 5'. The lower housing part 5' surrounds a sample collecting space 9', in which are arranged two cases 15' with sample collecting containers 17'. Filling of the sample collecting containers 17' occurs by means of a pivotable sample distributor arm 19', which is connected with the supply and metering system 21' described further below in greater detail. In the upper housing part 3', a cooling unit (not shown here) and an energy supply unit (likewise not shown) are, again, accommodated in a rear region of the housing part 3', which is separated from the metering space 11' by a partition. In a front region of the housing part 3' is arranged the electronics unit 7' with the control unit 31' and, separated from the electronics unit 7' by means of a partition 13', a metering space 11'. The metering space 11' is also essentially equally constructed to the metering space 11 of the sample taker 1 described earlier on the basis of FIGS. 1 and 2.

In contrast to the example of an embodiment described earlier, however, the sample taker 1' has a supply and metering system 21', which has a peristaltic pump functioning according to the peristaltic principle. The supply and metering system 21' includes a liquid-conveying, deformable hose 42. Via the hose connection 43 of the hose 42, the liquid sample is conveyed from a sample-taking location, and, via the hose connection 45, is fed to the sample distributor arm 19' through a feed-through in the partition between the upper housing part 3' and the lower housing part 5'. The peristaltic pump furthermore includes a drive element 41, which, during operation, is rotated by a pump drive secured to the rear-side of the plate 22' (and, consequently, not illustrated in FIGS. 4 and 5). During operation of the peristaltic-pump, the deformable hose 42 is subjected by means of the drive element 41 to peristaltic squeezing movements of predeterminable frequency in such a manner, that, pulsating in a predetermined flow direction, liquid which is located in the oscillating hose interior is conveyed, for example, from the hose connection 43 at the sample-taking location to the hose connection 45 at the sample distributor arm 19'.

Figure 5:
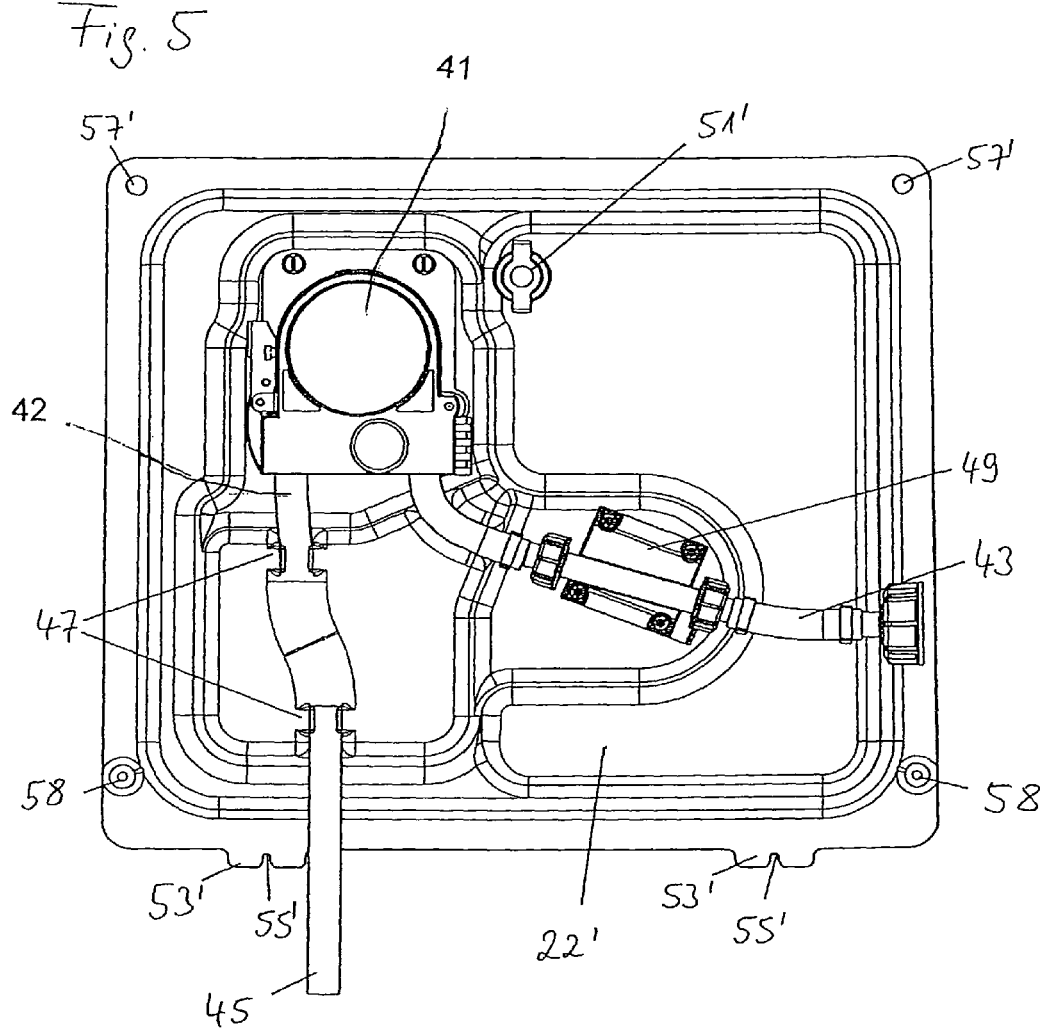
FIG. 5 is a schematically shown, detail view of the securement plate having the supply and metering system of the sample taker shown in FIG. 4.

FIG. 5 shows plate 22' in detail. Secured on the visible front side of the plate 22' in FIG. 5, are the drive element 41 and the hose 42. Plate 22' has a relief structure with raised portions and depressions, into which are embedded the components of the peristaltic supply and metering system 21' secured to plate 22'. For example, hose 42 is held between two clamp elements 47, which are formed in the relief structure of the plate. Further secured on plate 22' is a media detector 49, which serves to determine the volume of sample supplied by the hose 42. The media detector can be based, for example, on a pressure sensor, a strain gage or a flow sensor. Application of a pressure sensor for determining the volume of a liquid supplied by a peristaltic-pump is described in U.S. Pat. No. 6,871,551 B2, and will not be explained in detail here. Control unit 7' controls, among other things, the pump drive and the movement of the rotating sample distributor arm 19', using the measurement data received from the media detector 49. Plate 22' has an interface for its securement onto the housing part 3' of the sample taker 1' surrounding the metering space 11'. This interface is embodied identically to the interface for securing the plate 22 onto the corresponding housing part 3 of the sample taker 1 in the first example of an embodiment. The interface of the plate 22' thus includes protrusions 53' with grooves 55', which can be made to engage with complementary guiding rails of the housing wall of the housing part 3'. For affixing the plate 22', there is placed in the vicinity of the side of the plate opposite the plate side with the projections 53' a rotary latch 51', which can pivot behind a protrusion of the metering space housing forming a catch. The complementary cavities or the protrusion of the metering space housing can be formed directly in the housing wall of the housing part 3', or also by a structure connected with the housing wall. Additionally, plate 22' has bores 57', which serve as accommodations for elastic buffer elements, e.g. parabolic buffers. Furthermore, the plate 22' includes rear side depressions 58, which are visible in the front view of FIG. 5 as bulges, in which rear-side elastic buffer elements can be accommodated (compare with the representation in FIG. 6).

Figure 6:
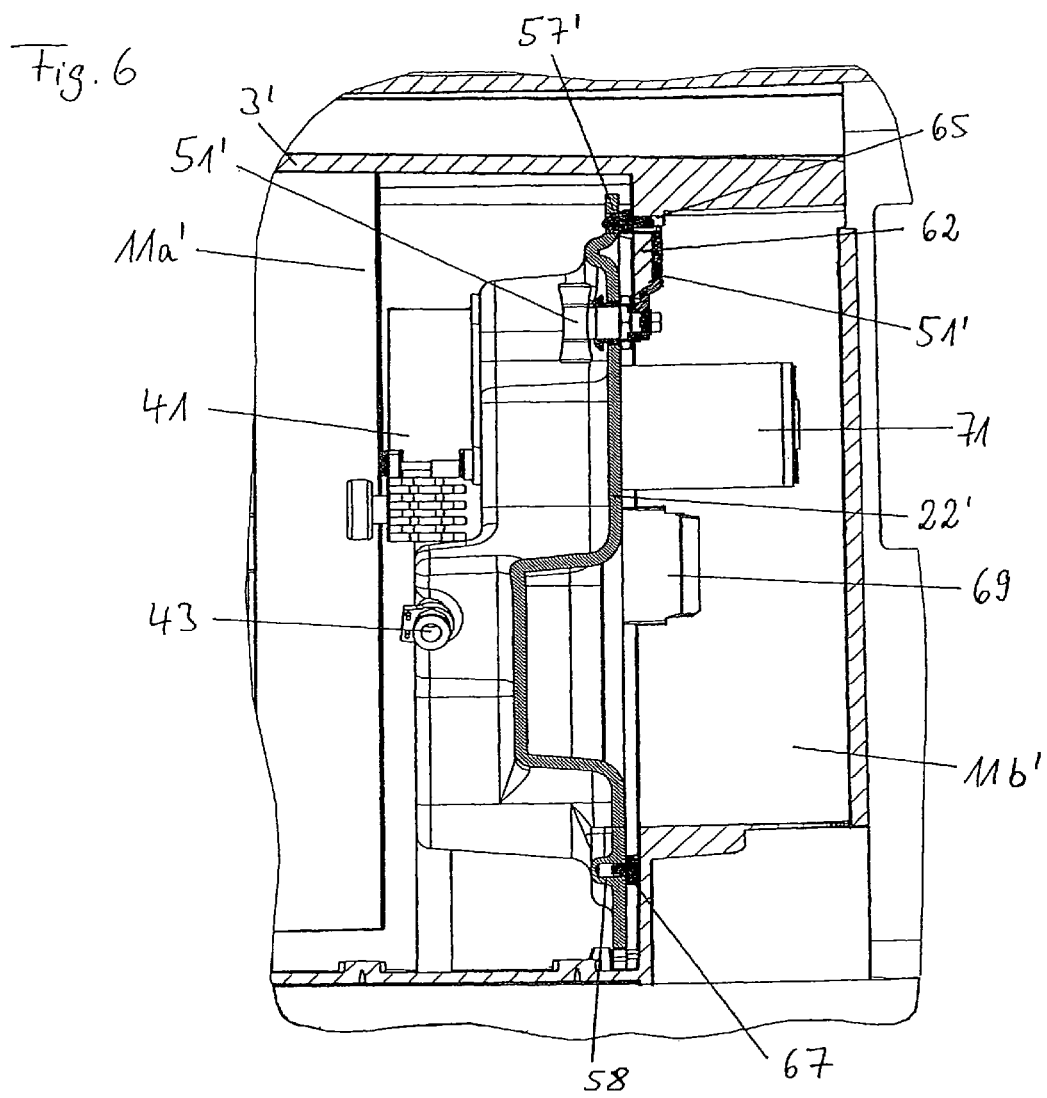
FIG. 6 is a schematically shown, detail view in cross section of the metering space with the securement plate of the sample taker shown FIG. 5.

FIG. 6 shows in a sectional illustration the plate 22' installed in the housing part 3' of the sample taker 1'. Recognizable is the relief structure of the plate 22'. Plate 22' divides the metering space 11' into a front metering space part 11a' and a rear metering space part 11b'. The rotary latch 51' is rotated behind the protrusion 62 of the upper inner wall of the housing part 3', and thus holds plate 22' firmly in position. Engaging in the bores 57' of the plate are parabolic buffer elements 65, which are seated in bores in the housing wall of the housing part 3'. Secured to the side of the plate 22' facing the second metering space part 11b' in a recess 58 is a buffer element 67, which presses against the housing wall.

Secured to the rear side of the plate is the pump drive 71 of the peristaltic supply and metering system 21'. The cross sectional presentation of FIG. 6 shows, moreover, the feed-through 69 between the housing part, which surrounds the electronics unit 7', and the rear metering space part 11a'. Extending through the feed-through 69 are electrical lines between the control unit 31' and components of the supply and metering system 21', e.g. the pump drive 71 or the media detector 49.

Figure 7:
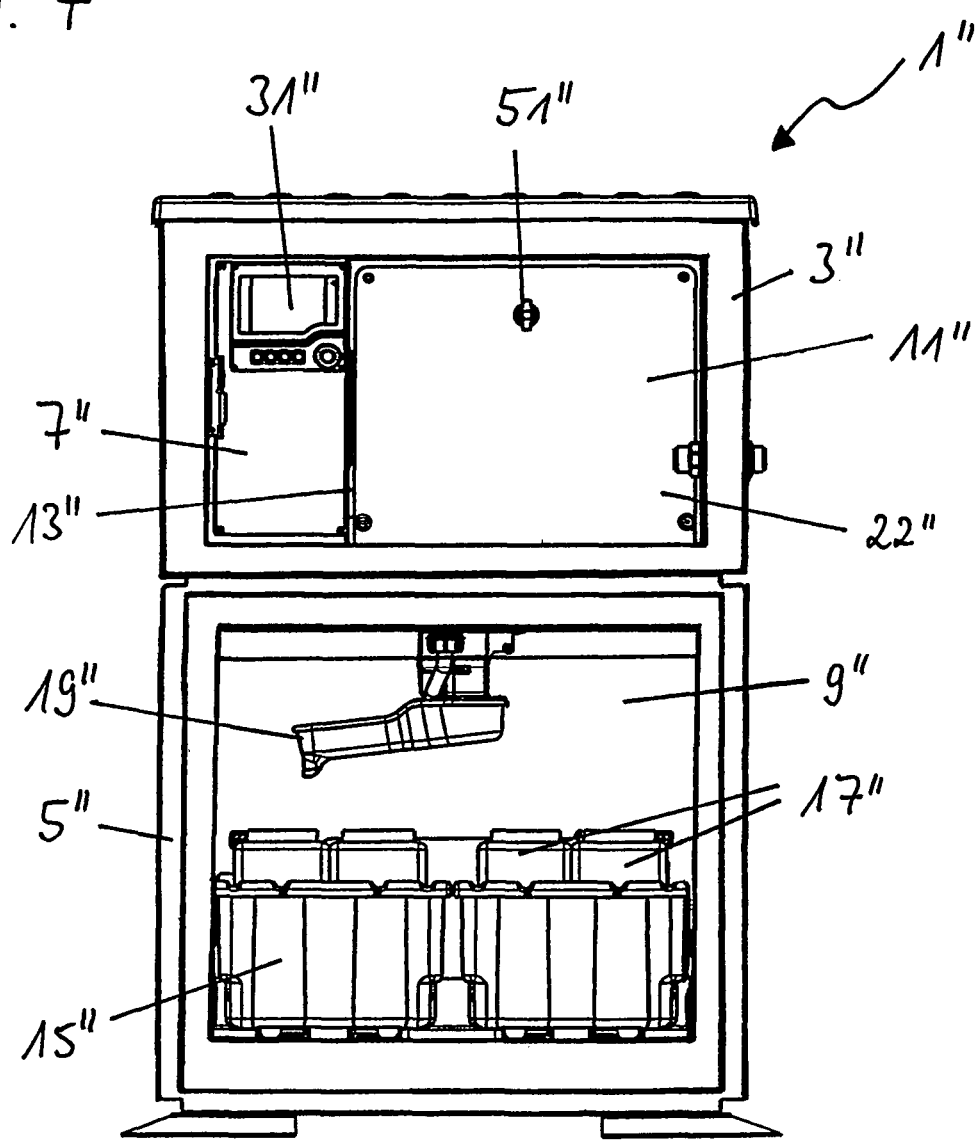
FIG. 7 is a schematically shown, total view from the front of a sample taker for removing samples from a media line under pressure.

FIG. 7 shows a total view from the front of an automatic sample taker 1" according to a third example of an embodiment. The sample taker 1" is constructed essentially equally to the sample takers of the previously described examples of embodiments. It includes an upper housing part 3" and a lower housing part 5". The lower housing part 5" includes a sample collecting space 9", in which two cases 15" with sample collecting containers 17" are arranged. The filling of the sample collecting containers 17" occurs by means of a pivotable, sample distributor arm 19", which is connected with a supply and metering system, which is described in greater detail below. In the upper housing part 3", a cooling unit (not shown here) and an energy supply unit (likewise not shown) are, again, accommodated in a rear region of the housing part 3". In a front region of the housing part 3" is arranged the electronics unit 7" with the control unit 31" and, separated by means of a partition 13" from the electronics unit 7", a metering space 11". The metering space 11" is also essentially equally constructed to the metering space 11 of the sample taker 1 described earlier on the basis of FIGS. 1 and 2, or to the metering space 11' of the sample taker 1' described on the basis of FIGS. 4 and 5.

A plate 22" divides the metering space 11" into a front metering space part and a rear metering space part (not visible in FIG. 7). In the example of an embodiment illustrated here, plate 22" is embodied as a blind plate, i.e. no components are secured on the front side of the plate which faces the front metering space part 11a'. The sample taker of the present example of an embodiment serves for removal of liquid samples from a media conveying pipe or housing (not shown), which is under elevated pressure. Consequently, for supplying the liquid samples, in the sample taker 1" only a valve mechanism is provided, which, together with the pipe, which is under pressure, or with the housing, forms, in the present example of an embodiment, the supply and metering system of the sample taker 1". Removal of liquid samples from the media-conveying pipe or vessel, either of which is under pressure, is controlled via the valve mechanism. The valve mechanism is arranged behind the plate 22" in the rear metering space part. The plate 22", which covers and seals the entire rear metering space part, protects the valve mechanism from environmental influences and especially from unauthorized accessing. The valve mechanism is controlled by the control unit 31".

FIG. 8 shows the blind plate 22" in detail. It includes an interface identical with that of the plates 22 and 22' presented in FIGS. 3 and 5 for securement to the inner wall of the housing part 3" surrounding the metering space 11". This interface thus includes protrusions 53" with grooves 55", which can be engaged with complementary guiding rails of the housing wall of the housing part 3. For affixing the plate 22", there is placed in the vicinity of the side of the plate opposite the plate side with the projections 53" a rotary latch 51", which can pivot behind a protrusion of the metering space housing wall. The complementary cavities or the protrusion of the metering space housing wall can be formed directly in the housing wall of the housing part 3, or also by a structure connected with the housing wall. Additionally, bores 57" are provided as accommodations for elastic buffer elements (e.g. parabolic buffers) which are connected with the housing 3". Rear side depressions 58" of the plate 22" serve to accommodate further elastic buffer elements.

Due to the identical embodiment of the interfaces for securing the plate 22, the plate 22' or the plate 22", it is possible, for example, to replace the plate 22', having the components of the supply and metering system 21' embodied as a peristaltic pump, with the plate 22 having the components of the supply and metering system 21 working according to the vacuum principle, or with the blind plate 22". This permits, on the one hand, the user of a sample taker of the embodiment according FIG. 1, FIG. 4 or FIG. 7 to retrofit the sample taker from one functional principle of the supply and metering system to another functional principle. On the other hand, with an identical basic construction of the sample taker, it is possible for the manufacturer to manufacture a sample taker with a functional principle of choice simply by using a plate provided with the parts of the corresponding supply and metering system. If other parts of the sample taker are embodied as modules, the manufacturer can provide a "module kit". By combining modules of various functionalities from the kit, the manufacturer can institute the manufacture of different sample takers very flexibly.

The plate 22", embodied as a blind plate, can also be used to secure supply and metering systems (or at least parts of these) which are manufactured for particular applications. Components of such supply and metering systems can, for example, be directly secured on the blind plate. This allows the manufacturer a still higher flexibility in the manufacture, since the manufacturer is thus not limited only to the available modules of the kit, but can also manufacture "special modules", which are simple to integrate into the basic sample taker structure.

The invention claimed is:

1. An apparatus for handling a liquid sample, comprising:
a control unit;
a sample collecting unit;
a supply and metering system which is embodied to convey a liquid sample from the sample-taking location and to meter the sample into a liquid receptacle of said sample collecting unit;
a housing with a first housing part, which at least partially surrounds at least said sample collecting unit, and a second housing part, which is separated from said first housing part, and which at least partially surrounds a metering space, said
at least parts of said supply and metering system are arranged in said metering space; and
a plate, which is releasably connected with said second housing part surrounding the metering space, and which divides the metering space into a first metering space part and a second metering space part.

2. The apparatus as claimed in claim 1, wherein:
at least parts of said supply and metering system are secured onto said plate.

3. The apparatus as claimed in claim 2, wherein:
all parts of said supply and metering system which are secured on said plate are arranged on a side of said plate facing said first metering space part.

4. The apparatus as claimed in claim 2, wherein:
said plate is embodied as a deep drawn part, which has a relief structure matched to the shape of the parts of said supply and metering system which are secured onto said plate.

5. The apparatus as claimed in claim 4, wherein:
said relief structure includes a cavity, in which is embedded and held a liquid line.

6. The apparatus as claimed in claim 1, wherein:
arranged in said second metering space part are other parts of said supply and metering system.

7. The apparatus as claimed in claim 1, wherein:
said plate is connected in at least three mounting points with said second housing part which surrounds the metering space part,
at least two mounting points are embodied as guiding means, which engage firmly into complementary guiding means, which are connected with said second housing part.

8. The apparatus as claimed in claim 7, wherein:
the third mounting point is embodied as a rotary latch, which can pivot behind a catch, which is formed in the inner wall of said second housing part surrounding said metering space, or which is firmly connected with said second housing part.

9. The apparatus as claimed in claim 7, wherein:
said plate, at at least two additional mounting points, lies floating on parabolic buffers relative to the wall of said second housing part.

10. The apparatus as claimed in claim 1, wherein:
said supply and metering system includes at least a peristaltic pump or a vacuum pump.

11. The apparatus as claimed in claim 1, wherein:
said sample collecting system is arranged in a separate sample collecting space, which is separate from said metering space.

12. The apparatus as claimed in claim 1, wherein:
there is on said plate furthermore a media detector, and/or a flow measuring device for determining volume (or a variable derived therefrom) of the liquid sample supplied by said supply and metering system.

13. A module kit for manufacturing an apparatus for handling a liquid sample comprising:
a control unit;
a sample collecting unit;
a supply and metering system which is embodied to convey a liquid sample from the sample-taking location and to meter the sample into a liquid receptacle of said sample collecting unit;
a housing with a first housing part, which at least partially surrounds at least said sample collecting unit, and a second housing part, which is separated from said first housing part, and which at least partially surrounds a metering space, said
at least parts of said supply and metering system are arranged in said metering space; and
a plate, which is releasably connected with said second housing part surrounding the metering space, and which divides the metering space into a first metering space part and a second metering space part:
an electronics unit, which includes said control unit,
wherein the first housing part, which at least partially surrounds the sample collecting unit, and is connected or connectable with additional housing parts for forming a housing of the apparatus;
a number of sets of components of various types of supply and metering systems, wherein said sets comprise at least a set of components of a supply and metering system which works according to a peristaltic principle, and a set of components of a supply and metering system which works according to a vacuum principle;
wherein said second housing part is connected or connectable with additional housing parts for forming a housing of the apparatus; and
a set of several differently embodied plates, each of which has, for forming the metering space, an identically embodied interface for releasably connecting the plate with the second housing part, wherein:
differently embodied plates have different relief structures, in order to accommodate different components or combinations of components of a supply and metering system and to secure them on the plate.

14. The module kit as claimed in claim 13, wherein:
the identically embodied interfaces comprise three mounting points, wherein at least two mounting points are embodied as guiding means, which can be made to engage with complementary guiding means, which are firmly connected with the second housing part.

* * * * *